United States Patent [19]
Storrs et al.

[11] Patent Number: 5,986,073
[45] Date of Patent: *Nov. 16, 1999

[54] METHOD FOR PURIFYING SOMATOTROPIN MONOMERS

[75] Inventors: Stephen B. Storrs, Glencoe, Mo.; Jeffrey S. Schorey, San Antonio, Tex.

[73] Assignee: Monsanto Company, St. Louis, Mo.

[*] Notice: This patent is subject to a terminal disclaimer.

[21] Appl. No.: 08/576,517

[22] Filed: Dec. 21, 1995

Related U.S. Application Data

[63] Continuation of application No. 08/332,607, Oct. 31, 1994, abandoned, which is a continuation of application No. 08/007,921, Jan. 25, 1993, abandoned, which is a continuation of application No. 07/486,476, Feb. 28, 1990, Pat. No. 5,182,369.

[51] Int. Cl.⁶ ............................................. C07K 1/30
[52] U.S. Cl. ................................... 530/419; 530/412
[58] Field of Search ...................... 530/412, 419

[56] References Cited

U.S. PATENT DOCUMENTS 5,182,369  1/1993  Storrs et al. .

*Primary Examiner*—Paula K. Hutzell
*Assistant Examiner*—Stephen Gucker
*Attorney, Agent, or Firm*—Gary M. Bond; Arnold, White & Durkee

[57] ABSTRACT

A method for purifying and recovering biologically active somatotropin monomers from refold solution following the solubilization and naturation of refractile bodies of host cells produced by recombinant DNA methodology. The purification process is based on the discovery that somatotropin monomers and somatotropin oligomers having overlapping isoelectric points may nevertheless be separated by selective precipitation over a narrow pH range. Host cell residues including proteins, pyrogens and other impurities present in the refold solution are effectively removed in the process. The purified somatotropin monomers recovered from solution after removing precipitated solids are suitable for parenteral application to target animals without further purification.

27 Claims, 3 Drawing Sheets

METHOD FOR PURIFYING SOMATOTROPIN MONOMERS

This application is a continuation of U.S. Ser. No. 08/332,607, filed Oct. 31, 1994, now abandoned, which was a Continuation of U.S. Ser. No. 08/007,921, filed Jan. 25, 1993, now abandoned, which was a Continuation of U.S. Ser. No. 07/486,476, filed Feb. 28, 1990, now Issued as U.S. Pat. No. 5,182,369.

FIELD OF INVENTION

This invention relates to the purification of somatotropin proteins produced by recombinant DNA technology, and more particularly, to the purification and recovery of somatotropin monomers by the separation and removal of somatotropin oligomers, residual host cell proteins and other impurities through a process of selective precipitation.

BACKGROUND OF INVENTION

Recombinant DNA technology has permitted the expression of heterologous protein in host cells such as *E. coli* bacteria. In the case of somatotropin, a growth hormone, the protein is sequestered in refractile bodies within the cytoplasm of the host cells. The refractile bodies may be recovered from the host cell culture by disrupting the cell so as to release the refractile bodies, and thereupon collecting the refractile bodies as a solid pellet by differential centrifugation. The refractile bodies are solubilized in an aqueous solution of a suitable chaotropic agent such as urea or guanidine hydrochloride at an alkaline pH, generally in the range of 10–12. The solubilized proteins are subsequently naturized by contact with a mild oxidizing agent to form intramolecular disulfide bonds and refold or return the protein to its biologically active native conformation. Methods for the solubilization and the naturation of somatotropin protein produced by *E. coli* bacteria using recombinant DNA technology are described in U.S. Pat. No. 4,511,502 and U.S. Pat. No. 4,652,630, each of which is incorporated herein by reference.

The refold solution obtained from the naturation step consists of an aqueous solution of somatotropin monomers, dimers and higher oligomers, with residues and other debris from the host cells. Of these, the somatotropin monomer is the desired biologically active agent and must be recovered in a highly purified form suitable for administration by injection to the target animal.

Purification of proteins is a common problem in biotechnology, and several methods to accomplish such purification have been developed. A literature survey entitled "Protein Purification: The Right Step at the Right Time" by J. Bonnerjea et al, reported in *Biotechnology*, Volume 4, pages 955–958 (November 1986) identified ten common methods for protein purification with ion exchange chromatography, affinity chromatography and gel filtration being the three most popular. As reported in this article, an average of four purification steps were necessary to purify proteins to homogeneity with an overall yield of 28% and a purification factor of 6,380. More than half the purification schemes were reported to include precipitation, generally as the first or second step after homogenation. The most popular scheme of purification was homogenization followed by precipitation, ion exchange chromatography, affinity separation and finally gel filtration. Precipitation was reported to produce an average purification factor of threefold.

Biologically active products derived from microbial sources and intended for parenteral use in animals must be substantially free from contaminating substances such as pyrogens, native microbial proteins and nucleic acids if they are not to initiate adverse reactions such as allergic response, fever and other side effects when administered. As reported in "Downstream Processing of Fermentation Products by Chromatography" by John M. Curling et al, *American Biotechnology Laboratory*, pages 33–37 (1983), traditional purification techniques such as precipitation technology which has been used since the 1950's for plasma fractionation are unable to achieve the high levels of purity that are required for recombinant DNA produced products. Of the high resolution purification techniques available to the biotechnology industry, chromatography is considered to be the method of choice at both research and production levels. The term "chromatography" includes the specific methods of ion-exchange, gel filtration, affinity chromatography, hydrophobic chromatography, and chromatofocusing. Chromatofocusing is a technique which separates proteins according to their isoelectric points in a resin bed having a pH gradient created by titrating a chromatographic gel with a specially prepared buffer.

Chromatography is reported to be the method of choice for commercial recovery of ultrapure human proteins and hormones from bacterial homogenates for therapeutic applications. The chromatographic purification is preferably preceded by an initial fractionation step such as protein precipitation or liquid-liquid partitioning to enrich the chromatographic feed stream and improve efficiencies as discussed in "Trends in Downstream Processing of Proteins and Enzymes" by P. Dunnill, *Process Biochemistry*, pages 9–13 (October 1983).

An example of the use of chromatography in the purification of prochymosin expressed from *E. coli* through DNA recombinant technology is described in "Synthesis of Calf Prochymosin (prorennin) in *Escherichia coli*" by J. M. Emtage et al, Biochemistry, Volume 80, pages 3671–3675 (June 1983). This reference also mentions that the majority of *E. coli* proteins (about 90%) precipitated under acidic conditions (pH 6.3) and could be removed by centrifugation.

Separation of proteins by precipitation techniques is discussed in "The Molecular Basis of Cell Structure and Function" by Albert L. Lehninger, *Biochemistry*, 2nd Edition, The John Hopkins School of Medicine (1975). This text explains that proteins in solution show profound changes in solubility as a function of pH, ionic strength, temperature and dielectric properties of the solvent, and that a protein is least soluble at its isoelectric pH, i.e., the pH at which the molecule has no net electric charge. Under such conditions, the protein molecules tend to coalesce and precipitate. Some proteins are virtually insoluble at their isoelectric pH and, as reported in this reference, where different proteins in solution have different isoelectric pH values, they can often be separated from each other by the method of isoelectric precipitation.

Purification by fractional precipitation based on pH adjustment is further discussed in *Biochemical Engineering Fundamentals*, Bailey and Ollis, 2nd Edition, pages 745–749 (1986). The method is suggested for separating proteins with different isoelectric points (pI), since at a given pH, proteins with the nearest pI will tend to precipitate, other things such as molecular weight being equal. By varying pH, fractions containing different proteins may be separated.

The solubility of proteins is affected by salt concentration and temperature of the solvent, and the resolution of precipitation fractionation may sometimes be improved by using salting out techniques and/or low temperatures to further reduce or enhance protein solubility. Isoelectric precipitation of low solubility proteins may also be improved by inclusion of a solute such as ethanol or acetone or an organic polymer such as polyethylene glycol in an aqueous medium. These techniques are discussed in *Protein Purification: Principles and Practice* by R. K. Scopes, 2nd Edition, pages 41–71 (1987). A classic example of the use of a salting out technique in a precipitation fractionation process mentioned in this reference is the one-step purification of glyceraldehyde phosphate dehydrogenase from rabbit muscle by precipitation at a pH above 7.5 and in an aqueous solution containing 3.2M ammonium sulfate.

As seen from the above discussion, precipitation fractionation is an old and well-known technique for obtaining some degree of separation and refinement of proteins in solution, and is an accepted method for making gross separations in order to enrich a feedstock for further processing and final purification by high resolution techniques such as chromatography. While specific conditions under which the precipitation fractionation is conducted can affect yield and purity of the resulting protein, the precipitation technique has not heretofore been utilized for final purification of proteins intended for parenteral administration by injection into target animals. Bovine somatotropin produced by recombinant DNA methodology for use in beef and dairy cattle, and the corresponding porcine somatotropin for use in raising hogs, have generally been purified by conventional chromatographic techniques. One such technique which involves subjecting impure protein stock solution to reverse phase purification on a macroporous acrylate ester copolymer resin support followed by elution with an organic diluent in aqueous solution at a pH between about 7 and 9 is described in U.S. Pat. No. 4,612,326.

The following additional U.S. patents are of interest for their disclosure of various protein purification techniques.

U.S. Pat. No. 3,239,418 describes a two-stage precipitation process followed by ion exchange to purify a pituitary growth hormone promoter.

U.S. Pat. No. 4,054,557 describes the purification of growth promoting polypeptides by gel filtration.

U.S. Pat. No. 4,426,323 describes a two-stage desalting and pH precipitation process wherein impurities are first removed by precipitation, following which the desired protein is precipitated and recovered.

U.S. Pat. No. 4,451,487 describes a process for the purification of biologically active proteins by the addition of a selected precipitation agent which promotes the precipitation of the desired protein while leaving impurities in solution.

U.S. Pat. No. 4,569,794 describes the purification of biologically active polypeptides and proteins by chromatographic techniques.

U.S. Pat. No. 4,617,376 describes a process for the purification of glucagon from a glucagon salt cake by hydrophobic chromatography.

Prior art chromatographic processes for the purification of proteins, including somatotropin proteins, are complex and expensive. Precipitation techniques, while relatively simple and inexpensive to operate, have not produced the yields and resolution required for products intended for parenteral use.

It is accordingly an object of the present invention to provide a method for purifying somatotropin proteins produced by recombinant DNA methodology.

It is a further object of this invention to provide a process for separating somatotropin monomers from somatotropin dimers and higher oligomers contained in solution.

It is a yet further object of this invention to provide a method for the isolation and recovery of somatotropin monomers from solutions containing somatotropin monomers and oligomers with residual host cell proteins and other contaminants.

A still further object of this invention is to provide an economical precipitation fractionation process for the recovery of high purity somatotropin monomers from the refold solution of the naturation step in a recombinant DNA process for the manufacture of somatotropin.

These and other objects and advantages of the present invention will be evident to those skilled in the art from the following description and examples.

SUMMARY

Briefly stated, the present invention provides a method for isolating and recovering biologically active somatotropin monomers from refold solution by selectively precipitating somatotropin dimer and higher oligomers together with residual host cell protein and other contaminating substances, leaving the desired monomer in solution. Precipitation is achieved by reducing the pH of the refold solution from initially high levels utilized in the solubilization and naturation steps to a pH end point generally in the range from about 4.5 to 6, at which pH substantially all the host cell protein and contaminant residues have precipitated, a major portion of the somatotropin oligomers have precipitated, and a major portion of the somatotropin monomers have remained in solution. Isoelectric focusing has shown that the somatotropin monomers are present as various "isoforms" having slightly different surface charges, and that these isoforms define three major groups having significantly different isoelectric points. Surprisingly, it has been discovered that effective separation of somatotropin monomers from oligomers by precipitation is possible even though the isoelectric points of these proteins lie in overlapping ranges. Furthermore, it has been discovered that there is no significant separation of the three major somatotropin monomer isoform groups even though these groups have significantly different isoelectric points.

After removing the precipitated solids from solution by filtration, centrifugation or other suitable means, the supernatant containing the solubilized somatotropin monomers is processed by diafiltration or other suitable means to concentrate the solution and remove buffer salts, following which the solution is dried to recover the purified somatotropin product. The purified product is substantially free of residual bacterial protein and other contaminants including pyrogens which cause adverse tissue reaction, and is suitable for direct administration to the target animal by injection or implantation without further purification by chromatography or other means generally employed prior to the present invention. The purified product may contain from less than 1% up to about 5% or more somatotropin oligomers which are biologically inactive and do not result in any adverse reaction when administered to the target animal.

The process is specifically demonstrated for N-methionyl bovine somatotropin (MBST), N-alanyl bovine somatotropin (ABST) and N-alanyl porcine somatotropin (PST).

DESCRIPTION OF INVENTION

Figure 1:
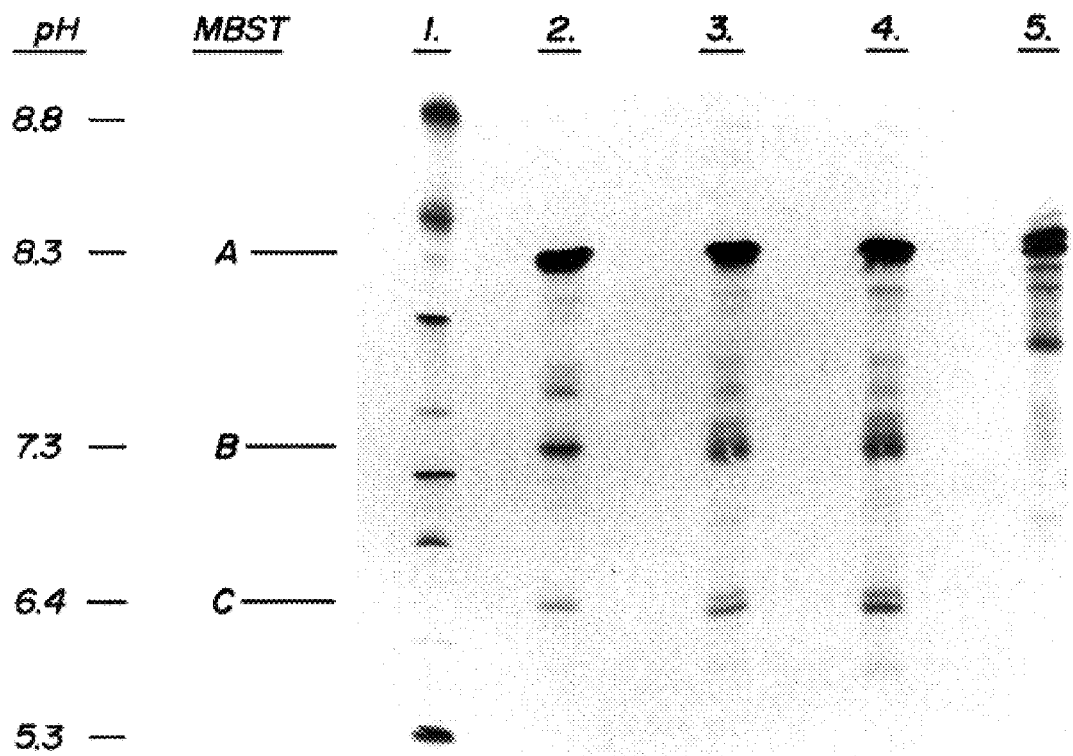
FIG. 1 is a photograph of an isoelectric focusing gel showing partially isolated MBST somatotropin proteins and illustrating the three major somatotropin monomer groups in lanes 3 and 4, identified as A, B and C and somatotropin dimer in lane 5.

For purposes of the present invention, the following terms should be considered to have the definitions listed below.

The term "somatotropin" is meant to include, but not be limited to, mammalian somatotropins such as human, ovine, porcine and bovine somatotropin, and others such as avian somatotropin. In addition to being suitable for the above somatotropin proteins having naturally occurring sequences, the present invention is equally applicable to systems involving analogs and homologs of the naturally occurring protein having somatotropin-like bioactivity. Accordingly, to the extent that such proteins are equivalents for purification purposes, the present invention includes such proteins.

"Heterologous" proteins are proteins which are normally not produced by the host cell. Recombinant DNA technology has permitted the expression of relatively large amounts of heterologous proteins such as somatotropin from transformed host cells, such as E. coli. However, while not fully understood, these foreign proteins are often sequestered in insoluble refractile bodies in the cytoplasm of the host cell.

By "refractile bodies" is meant the inclusion bodies or cytoplasmic aggregates containing, at least in part, the heterologous protein to be recovered. These aggregates appear as bright spots under a phase contrast microscope.

By "host cell" is meant a microbial cell such as bacteria and yeast or other suitable cell including animal and plant cells which has been transformed to express the heterologous protein. Host cells which are contemplated by the present invention are those in which heterologous somatotropin expressed by the cell is sequestered in refractile bodies. An exemplary host cell is E. coli K12, strain W3110G [pBGH1], which has been transformed to permit expression of bovine or porcine somatotropin.

"Naturation" refers to the folding and oxidation of the heterologous somatotropin protein to its native conformation to ensure biological activity.

"Folding" refers to the return of the overall conformational shape of the protein sufficient to permit proper oxidation. Folding is accomplished when the amino acid sequence of the protein is free to interact and assume its native secondary and tertiary structure.

"Oxidation" refers to the formation of the intramolecular disulfide bonds in the folded protein to stabilize the native conformation and ensure biological activity.

"Refold Solution" refers to the stock solution obtained as a result of the folding and oxidation in the naturation step.

The effectiveness of pH precipitation in separating somatotropin monomers from somatotropin oligomers does not conform to conventional theory regarding the separation of proteins based on differences in isoelectric points (pI). Somatotropin produced by recombinant DNA methodology includes three predominate monomer isoform groups having substantially different isoelectric points. Analytical isoelectric focusing (IEF) separates these monomer groups into distinct protein bands as illustrated for MBST in FIG. 1. The analytical IEF illustrated was performed on a flat bed electrophoresis apparatus. The gel contained 1% agarose, 10% sorbitol, 6M urea, and 2.5% pH 5–9 Ampholines; it was cast on FMC GelBond to a thickness of 1 mm. Focusing was performed for 135 min. at 15° C. with 10 watts constant power. The gel was fixed and stained to detect the focused proteins. Lane 1 contains Pharmacia standard IEF proteins; Lane 2 contains a highly purified MBST monomer standard prepared by chromatographic isolation; Lanes 3 and 4 contain MBST monomer purified by the method of the present invention; and Lane 5 contains highly purified, isolated MBST dimer. The MBST monomers in Lanes 3 and 4 comprise three major isoform groups labeled as A, B and C.

Further separation and analysis has demonstrated that the three somatotropin monomer isoform groups are common to N-methionyl bovine somatotropin (MBST), N-alanyl bovine somatotropin (ABST) and N-alanyl porcine somatotropin (PST). The relative proportions of these isoform groups and their approximate average isoelectric points, are presented in Table I below for representative samples of each somatotropin product:

TABLE I

| Monomer Isoform | Relative Proportion | Isoelectric Points |||
|---|---|---|---|---|
| | | MBST | ABST | PST |
| A | 2/3 | 8.3 | 8.5 | 7.3 |
| B | } 1/3 | 7.3 | 7.5 | 6.3 |
| C | | 6.3 | 6.5 | 5.0 |

Somatotropin dimers and higher oligomers are not found to have any well defined isoelectric point values but rather appear to be uniformly dispersed over the entire range of pIs reported for monomers (A), (B) and (C) above, as illustrated by the dimer of Lane 5 in FIG. 1.

In the following description and Examples, the purification process of the present invention is illustrated with reference to the purification of refold solution obtained by the solubilization and naturation of refractile bodies in aqueous urea as described in U.S. Pat. No. 4,652,630, it being understood that the invention is not limited by the specific details of the process used to produce the refold solution. For example, the urea used to solubilize refractile bodies may be replaced by other chaotropic agents such as guanidine hydrochloride, sodium thiocyanate and various detergents or by very high concentrations of sodium hydroxide. The naturation step may be conducted at lower pH values and/or with lower concentrations of the chaotropic agent than used in the solubilization step.

In the case of the solubilization and naturation process described in U.S. Pat. No. 4,652,630, the components of a typical refold solution will generally consist of from about 30–60% somatotropin monomers, from about 10–30% somatotropin dimer and higher oligomers, and from about 20–50% residues derived from the E. coli bacteria, including but not limited to, proteins, membrane fragments, color bodies, endotoxins, pyrogens and nucleic acids. In addition, the refold solution may contain urea at a concentration of from about 1.5 to 6M depending on the type of somatotropin being oxidized. As disclosed in U.S. Pat. No. 4,652,630, a urea concentration of between about 4 and 5M is preferred for naturation of bovine somatotropin, while a concentration of between about 2.5 and 3.5M is preferred for porcine somatotropin.

In a preferred embodiment of the present invention, the refold solution obtained from the naturation step is preconditioned if necessary before proceeding with the precipitation fractionation method of the present invention. In particular, if the solution contains a chaotropic agent such as urea or guanidine hydrochloride in sufficient quantity to interfere with the precipitation step, the concentration of the agent should be reduced to an acceptable level. In the case of urea, concentrations in excess of 3M have been found to increase the solubility of the somatotropins sufficiently to interfere with the is precipitation process. Accordingly, if the refold solution contains more than 3M urea, the concentration may be reduced by diafiltration or dilution to less than 3M and preferably to 1M or less. If the refold solution contains a chaotropic agent other than urea, such as for example guanidine hydrochloride, the minimum acceptable concentration for effective precipitation fractionation must be determined and the concentration adjusted accordingly if necessary.

As described in U.S. Pat. No. 4,652,630, naturation of solubilized somatotropin may be conducted at reduced temperatures such as 4° C. to retard degradation of urea. Temperature is not critical to the precipitation fractionation process of the present invention, however, and the refold solution may be allowed to warm to room temperature if desired. Warmer temperatures in the range of 20–25° C. may, in fact, offer slightly better oligomer separation.

In one embodiment of the precipitation process of the present invention, the pH of the refold solution is slowly reduced from the high level employed for the naturation step, usually in excess of pH 10, by slowly adding an acid, such as dilute acetic acid or other suitable organic or inorganic acid, with good mixing to avoid pockets of high acid concentration which would alter the pH equilibrium and have a localized effect on the solubility of the protein. The acid is added until a predetermined optimum pH end point value is reached. The optimum pH end point value must be determined individually for each protein system and will depend on variables such as relative proportions of somatotropin monomers and oligomers, the amount of bacterial proteins and contaminants present, and the presence or absence of various chaotropic agents, solvents, salts or solutes which affect the solubility of the proteins The optimum pH end point value is generally in the range of 4.5 to 6, and is identified as the pH at which substantially all the bacterial residues and associated contaminants have precipitated, a major portion of the somatotropin oliogomer has precipitated and the amount remaining in solution does not exceed maximum levels for acceptable degree of purity of the final product, and a major portion of the somatotropin monomer remains in solution and the amount which has precipitated does not exceed maximum levels for acceptable yields.

In general, process yields and final product purity are inversely related. Higher purities of the final somatotropin monomer product reflecting lower levels of oligomer are obtained at the expense of yield, and the maximum acceptable level of oliogomer is established by economical considerations. The somatotropin oligomers act as an inert diluent in the final product, diminishing the effective concentration of the active monomer component and requiring the gross dosage levels administered to the target animal to be increased accordingly. The oligomer is not believed to have any negative activity or to produce any undesirable side effect.

The actual relationship between yield and purity depends to some extent on the upstream conditions employed during the naturation step, and on the quality of feedstock being processed in the precipitation fractionation step. For refold solutions obtained from the solubilization and naturation of refractile bodies in urea as described above, the maximum acceptable level of somatotropin oligomer in the preferred purified somatotropin product has been established as 5% by weight, with the most desirable level being about 2.5% or less. The minimum acceptable yield for somatotropin monomer has been established at 50% with a desired yield of at least 65%. The optimum pH end point to obtain these results must be determined individually for each precipitation purification system, but generally in the range of 4.5 to 6, and most usually about 5.0 for MBST refold solutions when processed as described below.

Figure 2:
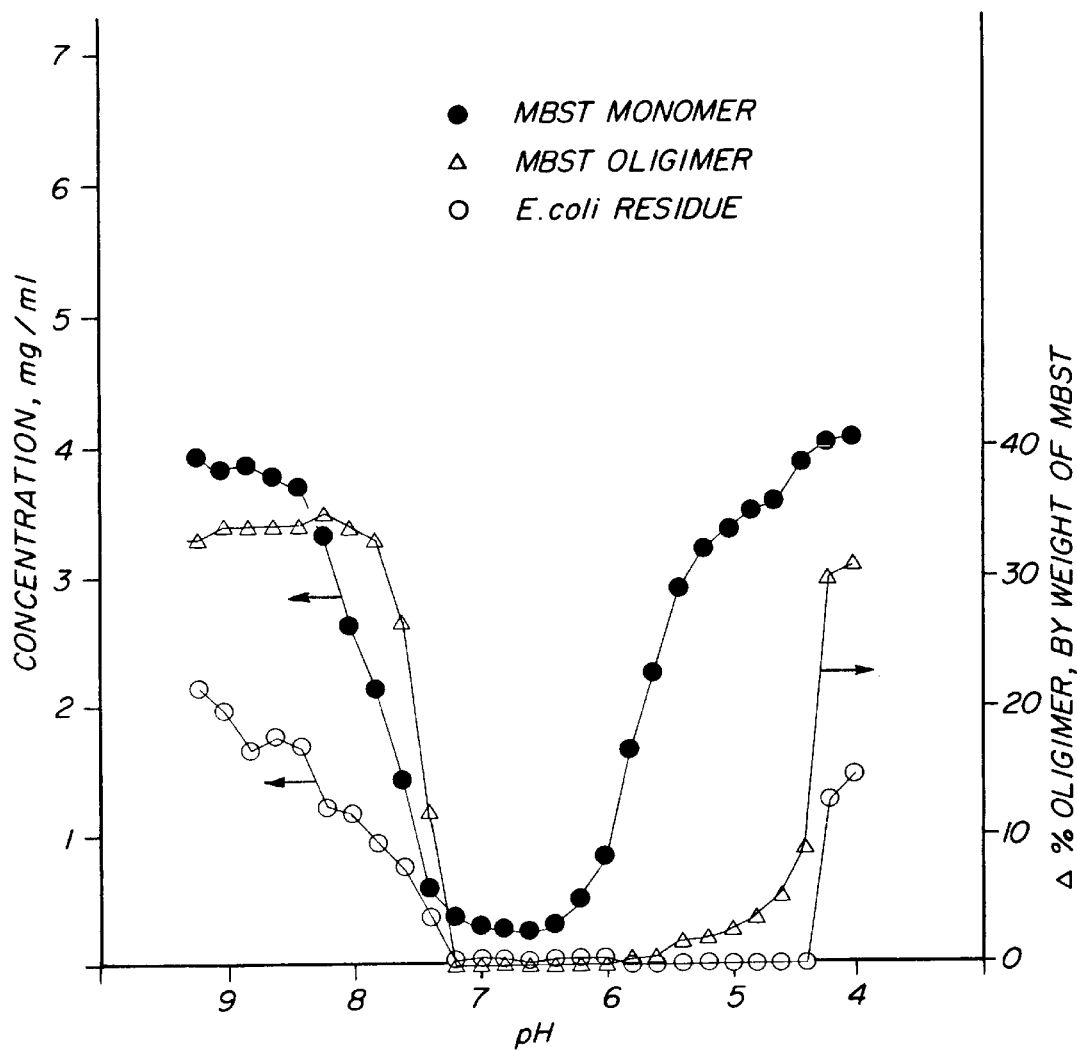
FIG. 2 is a solubility curve for MBST monomers, MBST oligomers and protein residue derived from E. coli.

The range for the optimum pH end point value of any given system can be predicted on the basis of protein solubility curves as illustrated for example in FIG. 2 which presents solubility data for the protein components of a representative MBST refold solution obtained from the urea system described above. As illustrated in this Figure, the residual proteins and impurities derived from *E. coli* are substantially totally precipitated over the pH range of from about 4.5 to 7.2. The amount of somatotropin oligomers in solution based on total MBST is less than 1% over a pH range of from about 5.5 to 7.2, but increases rapidly as the pH is reduced to less than 4.5. Somatotropin monomer has minimum solubility at a pH of about 6.5, and solubility increases rapidly as the pH is reduced to levels below 6. The optimum pH end point value for this particular system is about 5.0±0.2, at which pH the bacterial residues are substantially insoluble, the solubility of the somatotropin oligomers is about 2.5% resulting in a final MBST product purity of about 97.5%, and over 80% of the somatotropin monomers originally present in the system remain in solution to provide an acceptable yield.

Optimum end point pH and product yield and purity resulting from the precipitation process are influenced by the process conditions utilized in the naturation step, particularly refold pH, protein concentration and urea concentration. The data in Table II illustrate the effect of refold pH on optimum end point pH and precipitation yield to produce ABST containing 2% oligomer.

TABLE II

| Refold pH | Optimum End Point pH | Precipitation Yield, % |
|---|---|---|
| 11.4 | 4.8 | 87 |
| 11.1 | 5.2 | 76 |
| 10.7 | 5.4 | 58 |

The effect of somatotropin protein concentration during the naturation step on precipitation yield for ABST containing 2% oligomer, and for PST containing 2% oligomer, is illustrated the by the data in Table III.

TABLE III

| ABST | | PST | |
|---|---|---|---|
| Refold g/L | Precipitation Yield, % | Refold g/L | Precipitation Yield, % |
| 2.1 | 90 | 2.1 | 79 |
| 2.7 | 87 | 3.0 | 72 |
| 4.2 | 70 | 3.8 | 68 |
| 5.6 | 59 | 4.5 | 64 |

This effect of refold pH and protein concentration on the subsequent purification of the somatotropin monomers is believed to be due to higher levels of oligomers and/or other impurities being produced under refold conditions leading to lower precipitation yields. Thus, an important consideration in the method of the present invention is the quality of feed stock, and the solubilization and naturation steps should be operated in a manner consistent with other process considerations to maximize monomer yield and minimize the concentration of oligomers and other undesirable components which are to be removed by the method of the present invention.

Figure 3:
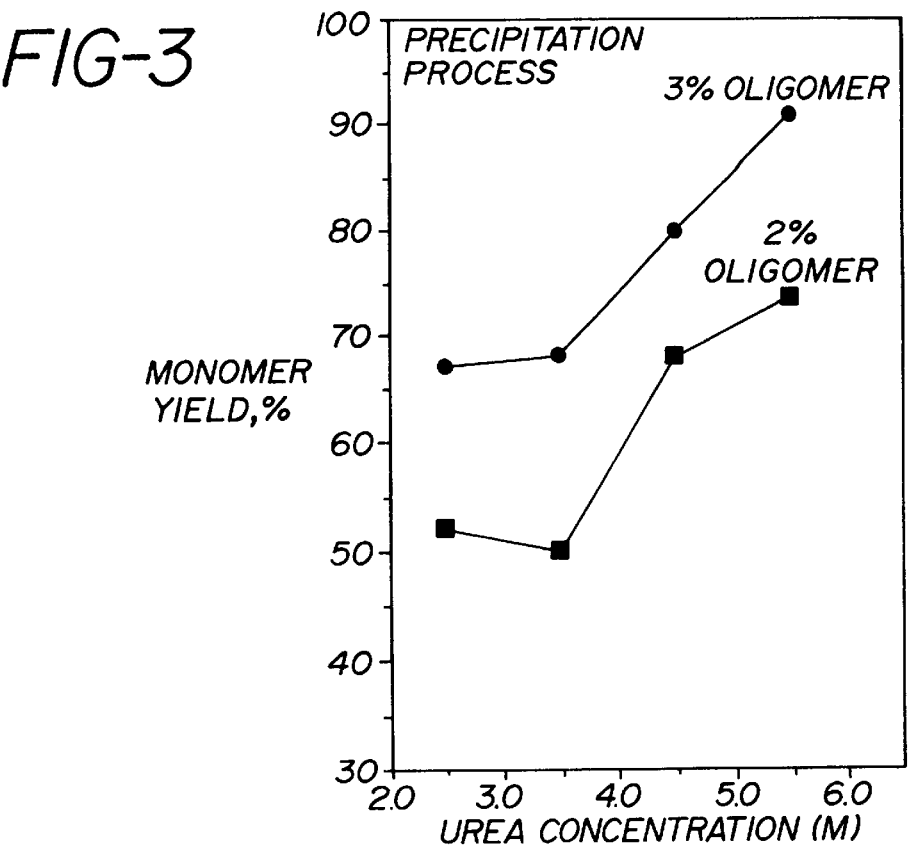
FIG. 3 illustrates the effect of refold urea concentration on yield of precipitation purification process for ABST.
Figure 4:
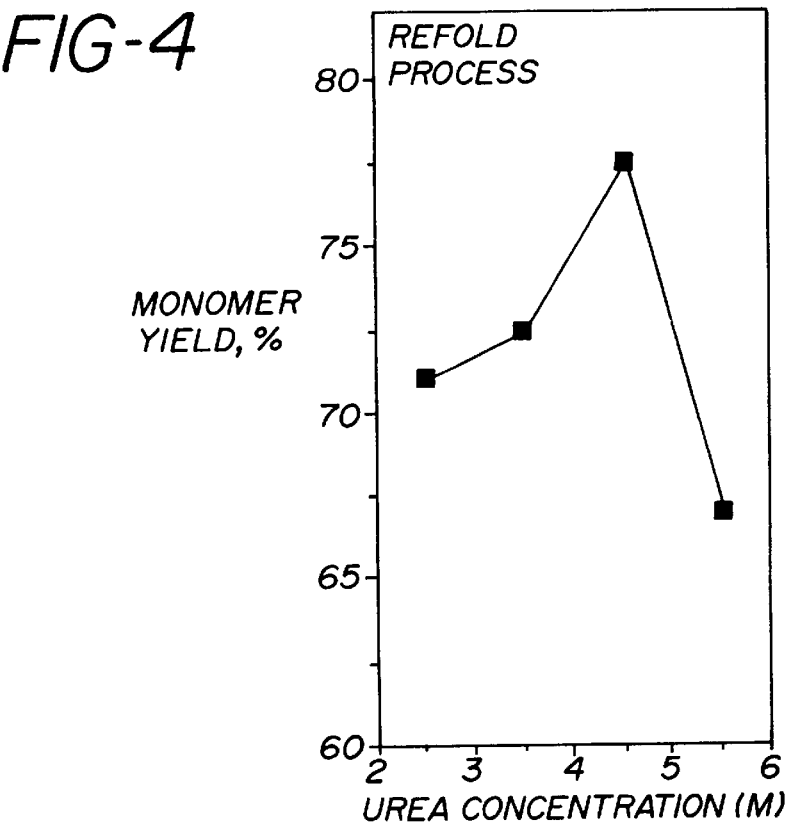
FIG. 4 illustrates the effect of refold urea concentration on yield of refold process for ABST.

The effect of refold urea concentration on precipitation yield for MBST is illustrated in FIG. 3, where yield of the final purification step is seen to increase as the concentration of urea employed in the naturation step is increased from 2.5M to 5.5M. However, as further illustrated in FIG. 4, product yield in the naturation step is maximum at 4.5M urea and decreases rapidly as the urea concentration is increased to 5.5M. Thus, overall process efficiency is a function of the individual yields at each step of the process, and the urea concentration during naturation must be selected to maximize total process yield. In the case of the system illustrated in FIG. 3 and FIG. 4, optimum urea concentration for the naturation step appears to be about 4.5M to maximize overall product yield.

The precipitation purification process of the present invention is illustrated by the following examples directed to the purification of N-alanyl bovine somatotropin and N-alanyl porcine somatotropin. All percentages are by weight.

EXAMPLE 1

Refractile bodies expressed in *E. coli* and containing N-alanyl bovine somatotropin (ABST) were prepared and isolated using known techniques. A sufficient quantity of refractile bodies were solubilized in 6 L of 4.5M aqueous urea at a pH of 11.25 and a temperature of 4° C. to provide a concentration of approximately 3.4 g/L ABST in solution. The refractile bodies dissolved quickly, and naturation of the resulting solution was conducted at 4° C. with stirring over a period of several days or until at least about 95% of the ABST oxidized and refolded to its native form. HPLC analysis of the oxidized refold solution indicated an ABST monomer yield of about 73%.

The refold solution was concentrated to 600 ml by diafiltration using a Millipore* PLGC 10,000 nominal M. W. limiting membrane, then exchanged with 5 volumes of cold D. I. water. The resulting solution contained approximately 25 g/L ABST monomer, 8 g/L ABST oligomers, 27 g/L *E. coli* residues and less than 0.2M urea in aqueous solution at about pH 10.

(* Millipore Corporation, 80 Ashby Rd., Bedford, Mass. 01730)

The solution thus prepared following conventional and known procedures was subsequently purified to recover the ABST monomer according to the method of the present invention as follows: 200 ml of the prepared solution was warmed to room temperature, and 5% acetic acid was added slowly over a period of 3 hours to lower the solution pH to 4.8 and cause a precipitate to form. The solution was maintained at pH 4.8 with stirring for 1 hour, then centrifuged to remove the precipitate. Analysis indicated the dissolved protein in the clear supernatant to contain 2.3% ABST oligomer and less than 0.01% *E. coli* residues as measured by ELISA, for an ABST monomer purity of 97+%. Yield of ABST monomer in the purification process was calculated at 83%. Purity of the ABST monomer was confirmed by SDS polyacrylamide gel electrophoresis.

EXAMPLE 2

Refractile bodies expressed in *E. coli* and containing N-alanyl porcine somatotropin (PST) were prepared and isolated using known techniques. A sufficient quantity of refractile bodies were solubilized in 2 L of 3M aqueous urea at a pH of 11.25 and a temperature of 4° C. to provide a concentration of approximately 3 g/L PST in solution. The refractile bodies dissolved quickly, and naturation of the resulting solution was conducted at 4° C. with stirring over a period of several days to permit the PST to oxidize and refold to its native form. HPLC analysis of the oxidized refold solution indicated a PST monomer yield of about 70%.

The refold solution was concentrated to 200 ml by diafiltration using a Millipore PLGC 10,000 nominal M. W. limiting membrane, then exchanged with 5 volumes of cold D. I. water. The resulting solution contained approximately 20 g/L PST monomer, 7 g/L PST oligomers, 15 g/L *E. coli* residues and less than 0.2M urea in aqueous solution at about pH 10.

The solution thus prepared following conventional and known procedures was subsequently purified to recover the PST monomer according to the method of the present invention as follows: 175 ml of the prepared solution to which had been added 8.75 g Celite 577 filteraid was warmed to room temperature, and 5% acetic acid was added slowly over a period of 1.75 hours to lower the solution pH to 4.7 and cause a precipitate to form. The solution was maintained at pH 4.7 with stirring for 1 hour, then centrifuged to remove the precipitate. Analysis indicated the dissolved protein in the clear supernatant to contain 2.6% PST oligomer and less than 0.01% *E. coli* residues as determined by ELISA for a PST monomer purity of 97+%. Yield of PST monomer in the purification process was calculated at 84.5%. Purity of the PST monomer was confirmed by SDS polyacrylamide gel electrophoresis.

In a variation of the above direct precipitation process, the optimum end point pH may be approached from the acid side by initially reducing the pH of refold solution to a level where substantially all the solubilized somatotropin monomer remains in solution, and thereafter increasing the pH to the optimum end point. With reference to the MBST solubility curve of FIG. 2, acetic acid may be added to cold refold solution at pH 10 to reduce the pH to less than about 4.5 At this pH level, all the solubilized proteins remain substantially soluble in the aqueous urea solution, and proteins which precipitated during the addition of the acetic acid are seen to redissolve as the pH is further reduced to less than 4.5. The concentration of urea or other chaotropic agent present in the solution may then be reduced to an acceptable level if appropriate by diafiltration or other suitable means. The pH is thereupon adjusted upward by the addition of NaOH or other suitable base until the optimum pH end point is attained as indicated by the precipitation of substantially all oligomers and *E. coli* protein while the MBST monomer remains in solution in good yield. The precipitate is removed and the purified MBST monomer recovered from solution as described above.

Feedstock quality and the efficiency of the precipitation purification process of the present invention may be improved in some cases by additional washing of the refractile bodies prior to the solubilization and naturation of the somatotropin proteins to remove contaminating cell debris. In certain instances, washing with water or aqueous solutions containing a detergent, solvent or NaOH may be helpful in removing many soluble impurities and result in an overall improvement in process yield and purity of the final somatotropin monomer product.

ALTERNATIVE EMBODIMENT - TWO STAGE PRECIPITATION

In an alternative embodiment of the present invention, the pH of the initial refold solution may be reduced beyond the optimum pH end point value to a point where at least about 80% the somatotropin monomer remains in solution, up to about 30% of the somatotropin oligomer remains in solution, and a minor portion of up to about 10% of the residual host cell protein remains in solution. The resulting precipitate is primarily composed of bacterial residues containing a substantial amount of somatotropin oligomer and is removed from the system by filtration or centrifugation, leaving an enriched solution of somatotropin monomer which preferably contains less than about 20% somatotropin oligomer and less than about 5% of bacterial residues based on total dissolved protein. The pH of this enriched solution is increased by the addition of NaOH or other suitable base to an optimum end point value at which point a major portion of the remaining somatotropin oligomer is precipitated along with substantially all of any host cell residues which are present, leaving a highly purified solution of somatotropin monomer. The advantage of this two step precipitation process resides in the fact that higher purities of somatotropin monomer can be obtained as a result of the enriched feedstock utilized in the second precipitation.

The two step precipitation process may be more readily understood by a reference to FIG. 2. As discussed above in connection with the single stage precipitation process, the optimum pH end point value for separation and recovery of the MBST monomer in this system was about 5.0±0.2, the pH at which substantially all the bacterial residues are precipitated and the concentration of the somatotropin oligomer remaining in solution is about 2.5%. By further reducing the pH to about 4.3, substantially all of the precipitated somatotropin monomer redissolves, while about 30% of the somatotropin oligomer redissolves with the concentration in solution increasing to about 10% by weight of MBST. The bacterial residues, however, remain substantially insoluble at this pH. Separation of the precipitate at this point removes substantially all the bacterial residues and approximately 70% of the somatotropin oligomer which was initially present in the system. The pH of the remaining solution is thereupon increased to the optimum end point value for the second precipitation, whereupon substantial further fractionation occurs with the precipitation of most of the remaining somatotropin oligomers and any residual bacterial proteins which may still be in solution. The optimum end point value for the second precipitation may not be the same as that for a single precipitation. In general, the optimum end point pH for the second precipitation will be in the range of 5.5 to 8.5 for bovine somatotropin, and between 5.5 and 7.5 for porcine somatotropin.

The two stage precipitation process is illustrated by the following Example.

EXAMPLE 3

200 ml of an MBST refold solution in 4.5M aqueous urea at pH 11 was dialyzed over 16 hours against approximately 50 L 1 mM NaOH at 4° C. whereby the concentration of urea was reduced to less than 0.2M. The solution was concentrated to 130 ml in an Amicon* stirred cell with YM10 membrane, at which point the solution contained approximately 7.0 g/L MBST monomer, 3.4 g/L MBST oligomer, and 2.1 g/L E. coli residual protein. The solution was warmed to room temperature, and the pH reduced by dropwise addition of dilute acetic acid to a value of 5.0, at which point significant precipitation occurred. The solution was centrifuged and the precipitate removed. The clear supernatant was collected and the pH adjusted to 6.0 by the addition of NaOH. After 1 hour, the sample was centrifuged to remove the second precipitate and the MBST monomer recovered in the clear supernatant. Purity and yield at each stage of the process were as shown in Table IV.

* Amicon Division, W. R. Grace & Co., Danvers, Mass. 01923

TABLE IV

| Stage | pH | % Oligomers | % Purity | % Yield |
| --- | --- | --- | --- | --- |
| 1 | 5.0 | 3.3 | ~96 | 95 |
| 2 | 6.0 | 0.5 | 99+ | 80 |
| | | overall process yield ~ 76% | | |

In the purification of MBST, the pH end point for the first precipitation is usually in the range of 4.0 to 5.5, while the pH end point for the second precipitation is usually in the range of 5.5 to 6.5. In the case of ABST, the first pH end point is usually in the range of 4.0–5.5 while the second pH end point is usually in the range of 6.5–8.5. In the case of PST, the first pH end point is usually in the range of 4.0–5.0 while the second pH end point is usually in the range of 5.5–7.5. In all cases the first pH end point is selected to precipitate a substantial portion of the somatotropin oligomers and E. coli residues while at least about 80%, and preferably 90 to 95% or more of the somatotropin monomer originally present remains in solution.

With the two stage precipitation process, the level of oligomers in the final product is readily reduced to less than 2% and often less than 1% with the final purity of the recovered somatotropin monomers being in excess of 99%.

While the preceding description and examples have been directed to specific somatotropin protein systems, it will be understood that the method of the present invention is generally applicable to the purification of MBST, ABST, PST and other variants of somatotropin. Optimum pH end point values and other process variables will depend on the specific conditions of the particular system but are readily determined from protein solubility curves and with minimal experimentation. The relative solubility of the protein in solution may be affected by temperature or the presence of various salts, solvents, solutes and the like, and the employment of such to increase differences in solubilities in order to enhance fractionation during the precipitation step is included in the scope of the present invention. Solvent modifiers which may be so used to enhance fractionation include alcohols such as ethanol and isopropyl, nonionic detergents such as Triton X-100 and Tween 80, polyethylene glycol, sugars, and various salts. Other elements of the process such as the acid or base used in making pH adjustments may be selected by the practioner according to individual preferences. The pH may be reduced, for example, using acetic, phosphoric, hydrochloric, sulfuric, nitric or citric acid, although the optimum pH end point may shift up or down slightly with different acids. The pH may be increased using NaOH, KOH, NH$_4$OH, tris(hydroxymethyl)amino methane or ethanolamine, although again the optimum pH end point may shift according to the particular base selected. All such process variables are included within the scope of the present invention.

We claim:

1. A method for the purification and recovery of biologically active somatotropin monomer which comprises
    a. obtaining a mixture of somatotropin proteins, the somatotropin selected from the group consisting of bovine somatotropin and porcine somatotropin, comprising biologically active somatotropin monomers and somatotropin oligomers in aqueous solution at a pH greater than about 7;
    b. selectively precipitating a major portion of somatotropin oligomers from said solution while maintaining a major portion of somatotropin monomers in solution by reducing the pH of said solution to a pH endpoint less than 6.5; and c. removing the precipitate to recover the somatotropin monomers remaining in solution.

2. The method of claim 1 wherein the obtained mixture of somatotropin proteins comprises a major portion of somatotropin monomers and a minor portion of somatotropin oligomers.

3. The method of claim 2 wherein the somatotropin oligomers are present in an amount of from about 10 to 30% by weight of total protein.

4. The method of claim 3 wherein the amount of somatotropin oligomers remaining in solution after precipitation is less than about 5% by weight of the total somatotropin protein remaining in solution.

5. The method of claim 1 wherein the obtained mixture of somatotropin proteins are in aqueous solution at a pH greater than about 10.

6. The method of claim 5 wherein said somatotropin oligomer is preferentially precipitated by reducing the pH of said solution to an end point value in the range of from about 4.5 to 6.

7. The method of claim 1 including the further step of removing volatiles from the recovered solution to obtain a dry somatotropin protein product. pin.

8. The method of claim 1 wherein the somatotropin protein is bovine somatotropin.

9. The method of claim 8 wherein the somatotropin is N-methionyl or N-alanyl bovine somatotropin.

10. The method of claim 1 wherein the somatotropin is N-alanyl porcine somatotropin.

11. A method for the purification and recovery of biologically active somatotropin monomer, which comprises a. obtaining a mixture of somatotropin proteins, the somatotropin selected from the group consisting of bovine somatotropin and porcine somatotropin, comprising somatotropin monomers, somatotropin oligomers and bacterial residues in aqueous solution at a pH greater than about 7;

b. selectively precipitating a major somatotropin of somatotropin oligomers and bacterial residues from said solution while maintaining a major portion of somatotropin monomers in solution by reducing the pH of said solution to a pH endpoint less than about 6.5; and c. removing the precipitate to recover the purified somatotropin monomers remaining in solution.

12. The method of claim 11 wherein the mixture of proteins in solution is obtained from the naturation of somatotropin protein produced from host cell cultures by recombinant DNA methodology.

13. The method of claim 12 wherein said bacterial residues are derived from *E. coli* host cells.

14. The method of claim 11 wherein a major portion of said bacterial residues are preferentially precipitated with the somatotropin oligomers.

15. The method of claim 11 wherein said obtained solution comprises at least about 30% somatotropin monomers, from about 10 to 30% somatotropin oligomers and from about 20 to 50% bacterial residues.

16. The method of claim 15 wherein the protein remaining in solution after precipitation comprises at least about 95% somatotropin monomers, less than about 5% somatotropin oligomers and less than about 1% bacterial residues.

17. The method of claim 11 including the further step of removing volatiles from the solution remaining after precipitation to obtain a dry somatotropin protein product.

18. The method of claim 11 wherein said aqueous solution includes a chaotropic agent.

19. The method of claim 18 wherein said chaotropic agent is selected from the group consisting of urea, guanidine hydrochloride, sodium thiocyanate and detergents.

20. The method of claim 18 wherein said chatropic agent is urea, and the concentration of said urea during the precipitation step is less than about 3M.

21. The method of claim 20 wherein the obtained mixture of proteins are in aqueous solution at a pH greater than about 10.

22. The method of claim 21 wherein the said somatotropin oligomers and bacterial residues are preferentially precipitated by reducing the pH of said solution to an end point value between about 4.5 and 6.

23. The method of claim 11 wherein the somatotropin protein is bovine somatotropin.

24. The method of claim 23 wherein the somatotropin is N-methionyl or N-alanyl bovine somatotropin.

25. The method of claim 11 wherein the somatotropin is N-alanyl porcine somatotropin.

26. A method for the purification and recovery of biologically active somatotropin monomer which comprises a. obtaining a mixture of somatotropin proteins comprising biologically active somatotropin monomer and somatotropin oligomer, both monomer and oligomer having intramolecular disulfide bonds, in aqueous solution at a pH greater than about 7;

b. reducing the pH of said solution to a pH end point less than 6.5 effective for selectively precipitating a minor portion of somatotropin monomer and a major portion of the somatotropin oligomer from said solution while maintaining a major portion up to about 90% by weight of the somatotropin monomer in solution; and c. removing the precipitate to recover the somatotropin monomer remaining in solution.

27. A method for the purification and recovery of biologically active somatotropin monomer which comprises a. obtaining a mixture of proteins comprising biologically active somatotropin monomer and somatotropin oligomer, both monomer and oligomer having intramolecular disulfide bonds, and bacterial residues in aqueous solution at a pH greater than about 7;

b. reducing the pH of said solution to a pH end point less than about 6.5 effective for selectively precipitating a minor portion of somatotropin monomer and a major portion of somatotropin oligomer and a major portion of bacterial host cell protein leaving only up to about 10% of bacterial host cell protein in said solution while maintaining a major portion of the somatotropin monomer in solution; and c. removing the precipitate to recover the purified somatotropin monomer remaining in solution.

\* \* \* \* \*

NITED STATES PATENT AND TRADEMARK OFFICE
CERTIFICATE OF CORRECTION

PATENT NO. : 5,986,073

DATED : November 16, 1999

INVENTOR(S) : Stephen B. Storrs and Jeffrey S. Schorey

It is certified that error appears in the above-identified patent and that said Letters Patent is hereby corrected as shown below:

Claim 7, Column 13, line 26, after "product." delete "pin."

Signed and Sealed this

Eighteenth Day of July, 2000

Attest:

Attesting Officer

Q. TODD DICKINSON

*Director of Patents and Trademarks*